United States Patent [19]
Tanihata

[11] Patent Number: 6,159,185
[45] Date of Patent: Dec. 12, 2000

[54] AUTOMATIC SAMPLING DEVICE WITH A SYRINGE

[75] Inventor: Hiroshi Tanihata, Kyoto, Japan

[73] Assignee: Shimadzu Corporation, Kyoto, Japan

[21] Appl. No.: 09/158,112

[22] Filed: Sep. 22, 1998

[30] Foreign Application Priority Data

Nov. 14, 1997 [JP] Japan ..................................... 9-312935

[51] Int. Cl.[7] .............................. A61M 5/32; A61M 5/00; A61B 5/00; B65D 81/00
[52] U.S. Cl. .......................... 604/198; 604/263; 604/187; 600/578; 600/576
[58] Field of Search ..................................... 604/187, 192, 604/198, 199, 263, 110, 117; 128/760, 763, 764, 765, 766, 768, 770, 772; 600/573, 576, 578, 577, 579

[56] References Cited

U.S. PATENT DOCUMENTS

| | | | |
|---|---|---|---|
| 5,092,461 | 3/1992 | Adam | 206/365 |
| 5,125,908 | 6/1992 | Cohen | 604/196 |
| 5,295,972 | 3/1994 | Mischenko | 604/192 |
| 5,599,310 | 2/1997 | Bogert | 604/164 |
| 5,817,074 | 10/1998 | Racz | 604/272 |

*Primary Examiner*—Mark O. Polutta
*Assistant Examiner*—Kelly M Cheney
*Attorney, Agent, or Firm*—Kanesaka & Takeuchi

[57] ABSTRACT

An automatic sampling device is formed of a syringe with a hollow needle, a plug formed of a soft elastic member and slidably engaging the needle to cover at least an opening of the needle, and a guide mechanism situated between the plug and the syringe. The guide mechanism holds the plug to allow the plug to hold the tip of the needle along a center axis of the syringe and to allow the needle to move through the plug from the tip to a root of the needle. When the tip of the needle is located in the plug, the opening of the needle is closed to prevent passage of a fluid therethrough. Thus, a sample gas does not leak through the opening of the needle due to diffusion. Also, since the mechanism for holding the rubber plug provided at the needle tip also acts as the guide for holding the needle tip on the center axis of the syringe, the needle does not generally bend even if a force in an oblique direction is applied to the needle tip.

6 Claims, 5 Drawing Sheets

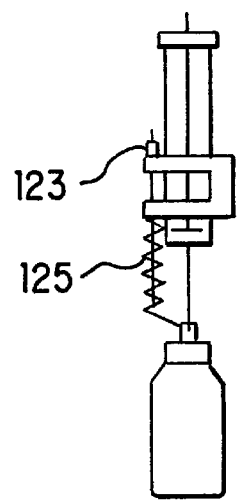
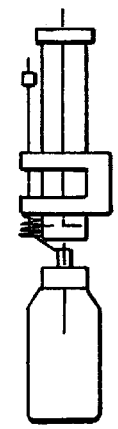
FIG. 2(a)   FIG. 2(b)
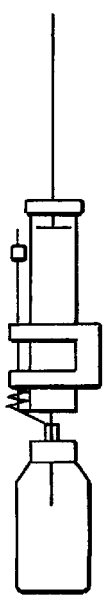
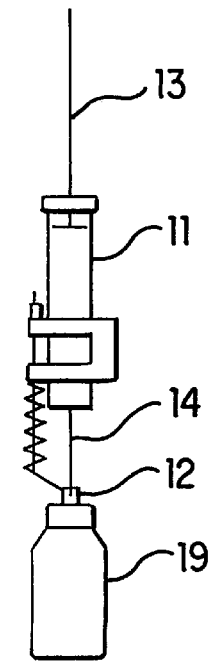
FIG. 2(c)   FIG. 2(d)

AUTOMATIC SAMPLING DEVICE WITH A SYRINGE

BACKGROUND OF THE INVENTION AND RELATED ART STATEMENT

The invention relates to an automatic sampling device or auto-sampler to be used in a gas chromatograph or the like, in particular a syringe mechanism suitable for automatically sampling a gas.

In a gas chromatography, a syringe is often used for introducing an analyzing sample into a gas chromatograph. In this method, at first, a predetermined amount of a sample is sacked from a sample container capped with, for example, a rubber septum by means of a syringe. Then, a needle of the syringe is inserted into a rubber septum covering a sample pouring opening of the gas chromatograph, and the sucked sample is pored into the pouring opening.

However, there have been several problems in using the conventional syringe.

First, since an opening of a hollow needle of the syringe is open, especially after a gas is taken therein, during a period from a time when the gas is taken by the syringe to a time when the gas is poured or supplied into the pouring opening of the gas chromatograph, the gas may leak out of the opening of the needle due to diffusion, or on the contrary, air may enter therein to thereby decrease an accuracy of the sampling.

As a countermeasure for the problem, a syringe valve to be mounted between a barrel and the needle of the syringe has been developed. However, in case the syringe valve is used, a dead space is increased, or the sample or air entering into a minute portion of the valve may interrupt the next sampling. In other words, contamination is liable to take place. Also, as a simple solution, there has been developed a needle cap formed of a small soft plastic member for covering a tip of the needle. However, in this case, a troublesome labor for attaching or detaching the needle cap is required whenever a sampling is carried out.

Further, there is a serious problem that both the syringe valve and needle cap can not be applied to the automatic sampling device. More specifically, it is difficult to automatically open or close the valve mounted on a part of the syringe, or automatically attach or detach the cap to or from the tip of the needle by a machine. Even if the syringe valve and needle cap could be applied to the automatic sampling device by some complicated mechanism, reliability of the movement would not be expected. Thus, applications of the valve and cap to the automatic sampling device are practically impossible.

A second problem in sampling by the syringe is a bending or breaking of a needle. In case the needle of the syringe is inserted into the septum covering the pouring opening of the gas chromatograph, since the septum is generally very hard, and a septum made of a special material wherein a heat resisting property is increased to suppress a bleeding is especially very hard, a large force has to be applied to the needle linearly in the axial direction of the syringe. If a force slightly deviated from the axis direction is applied, there is a risk of bending the needle. Especially, an unexperienced user is liable to fail to thereby bend the needle.

Accordingly, an object of the invention is to provide an automatic sampling device, wherein in case a gas sampling operation is carried out, leakage of the gas from an opening of a needle due to diffusion of the gas can be prevented.

Another object of the invention is to provide an automatic sampling device as stated above, wherein bending of the needle can be prevented when the needle is inserted into a septum covering a pouring opening of a sample bottle.

Further objects and advantages of the invention will be apparent from the following description of the invention.

SUMMARY OF THE INVENTION

An automatic sampling device of the invention has a syringe for analysis and is used in a gas chromatograph, especially suitable for automatically sampling a gas. The syringe of the automatic sampling device includes a guide for holding a tip of a needle on a center axis of the syringe; a guiding mechanism for moving the guide in an area from the tip to a vicinity of a root of the needle; and a plug formed of a soft elastic member (hereinafter referred to simply as "rubber plug") with the needle inserted thereinto, and moving along the needle together with the guide.

Although the needle tip is normally inserted into the rubber plug to close an opening of the needle, in case the needle tip covered with the rubber plug is inserted into an object, for example, a septum covering a pouring opening of a sample bottle, when the needle tip covered with the rubber plug is subjected to abut against the septum and is then pushed further, the needle penetrates through the rubber plug and pierces the septum, and the rubber plug is pushed toward a root of the needle. After the needle is pulled out of the septum, the rubber plug is returned to the tip of the needle by a force of a spring or the like to thereby close the opening of the needle. Since the mechanism for holding the rubber plug at the tip of the needle also functions as the guide for supporting the needle tip along the central axis of the syringe, even if a force in an oblique direction is applied to the needle tip, the needle does not easily bend.

BRIEF DESCRIPTION OF THE DRAWINGS

FIG. 1(*b*) is a sectional view taken along line 1*b*—1*b* in FIG. (*a*);

FIGS. 2(*a*) to 2(*d*) are explanatory side views for showing steps of movements of the syringe;

FIG. 3(*b*) is a sectional view taken along line 3*b*—3*b* in FIG. 3(*a*);

FIG. 5(*b*) is an enlarged sectional view for showing a structure of a needle tip portion inserted into a rubber plug.

DETAILED DESCRIPTION OF PREFERRED EMBODIMENTS

Figure 1A:
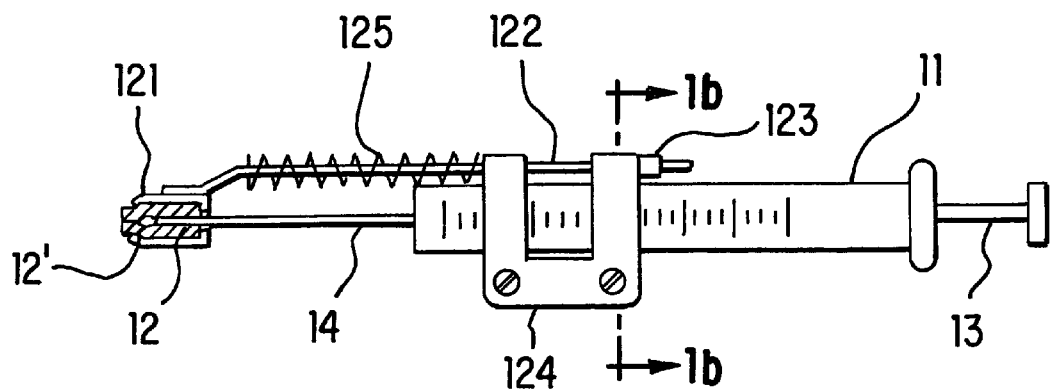
FIG. 1(*a*) is an explanatory side view for showing a syringe of a first embodiment of the invention.
Figure 1B:
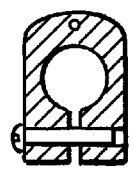

FIG. 1(*a*) shows a first embodiment of a syringe of an automatic sampling device according to the present invention, wherein reference numeral 11 represents a barrel of the syringe; 13 is a plunger; and 14 is a needle. A conventional syringe for an automatic sampling device is basically formed of the above-mentioned three elements. Since the barrel 11 has a cylindrical shape, it has an imaginary center axis, and the plunger 13 and the needle 14 are located on the imaginary center axis or an extended line thereof (hereinafter, simply referred to as "center axis"). Incidentally, FIG. 1(b) is a sectional view of a guide holder 124 taken along line 1b—1b in FIG. 1(a).

In addition to the three elements of the conventional syringe of the automatic sampling device, the syringe of the present embodiment according to the invention includes a rubber plug 12, rubber plug socket 121, guide bar 122, stopper 123, guide holder 124 and spring 125.

More specifically, the cup-shape rubber plug socket 121 has a small hole at a bottom center thereof, which functions as a needle guide for holding a tip of the needle 14 inserted thereinto on the center axis of the syringe. The cylindrical rubber plug 12 held in the socket 121 has a through-hole 12' with an inner diameter slightly smaller than an outer diameter of the needle 14 on its center axis, and can slide from the tip to a vicinity of a root of the needle inserted thereinto. Since an inner diameter of the rubber plug socket 121 is slightly smaller than an outer diameter of the rubber plug 12, the rubber plug 12 inserted thereinto is compressed to be firmly held. Also, since the hole of the rubber plug is squeezed to close, an opening at a tip of the needle 14 inserted into the rubber plug hole is closed. By slightly bending the opening of the rubber plug socket 121 inwardly to be smaller in its diameter, the needle opening is more effectively closed and, at the same time, the rubber plug is prevented from falling out of the socket.

The guide bar 122 made of a tough and hard material, such as stainless steel, is welded at one end to the rubber plug socket or needle guide 121, and inserted at the other end into openings of the guide holder 124 fixed to the barrel 11, so that the guide bar 122 slides parallel to the barrel 11. Numeral 123 represents a stopper adjustably fixed to a vicinity of an end of the guide bar 122 by a screw or the like, and 125 is a spring.

Operations for taking out a sample from a sample bottle 19 with a septum cap by the syringe shown in FIG. 1 are described with reference to FIGS. 2(a)–2d.

First, the barrel 11 of the syringe is firmly held, and an edge of the rubber plug 12 is pushed against the septum cap by moving the syringe.

When a force is further added thereto, the needle 14 passes through the rubber plug 12 and pierces the septum cap to thereby enter into the sample bottle 19 FIG. 2(b). At this time, the rubber plug 12 is pushed by the septum cap and moved toward the root of the needle, and the spring 125 is compressed.

Then, the plunger 13 is drawn out to suck the sample into the barrel 11 FIG. 2(d).

When the barrel 11 is pulled to take out the needle 14 from the sample bottle 19, the rubber plug 12 is returned to a vicinity of the tip of the needle by the action of the spring 125 to thereby close the opening of the needle FIG. 2(d). At this time, the stopper 123 functions to prevent the rubber plug 12 from falling out of the tip of the needle.

As described hereinabove, in case the syringe of the invention is used, in a state where the needle is drawn out of an object, such as the septum of the sample bottle, the rubber plug 12 is located to cover the tip of the needle to close the needle opening, so that the sample sucked into the syringe is prevented from being dispersed from the needle opening. Also, under this condition, since the tip of the needle is held on the center axis of the syringe by a mechanism including the rubber plug 12, rubber plug socket or needle guide 121 and guide bar 122, there is no risk of the needle being bent when the needle is pierced into the object.

Incidentally, since the spring 125 functions to push the needle 14 of the syringe inserted into the sample bottle 19 backwardly under the states shown in FIGS. 2(b) and 2(c), the operations may not work properly. In such a case, the spring 125 may be omitted. In case the spring 125 is omitted, in the operation process from FIG. 2(c) to FIG. 2(d), if the needle is drawn out by one hand while pressing the sample bottle 19 and the rubber plug 12 with the other hand, since the rubber plug 12 automatically returns to the tip of the needle, there is almost no problem in use. However, in case the present invention is applied to an automatic sampling device, described later, mechanical means, such as a spring, is required to return the rubber plug to the tip of the needle. In other words, the spring 125 is not an essential element of the invention, and may be provided, if necessary.

Figure 3A:
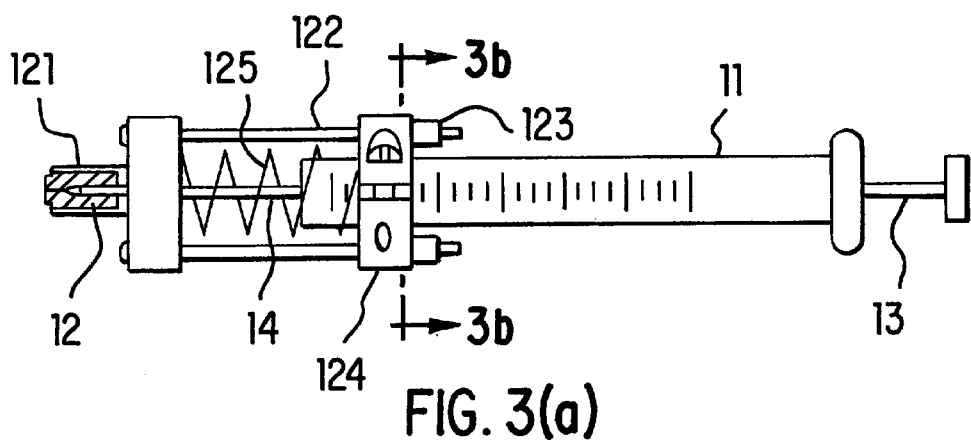
FIG. 3(*a*) is an explanatory side view for showing a syringe of a second embodiment of the invention.
Figure 3B:
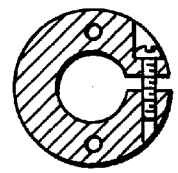
Figure 4:
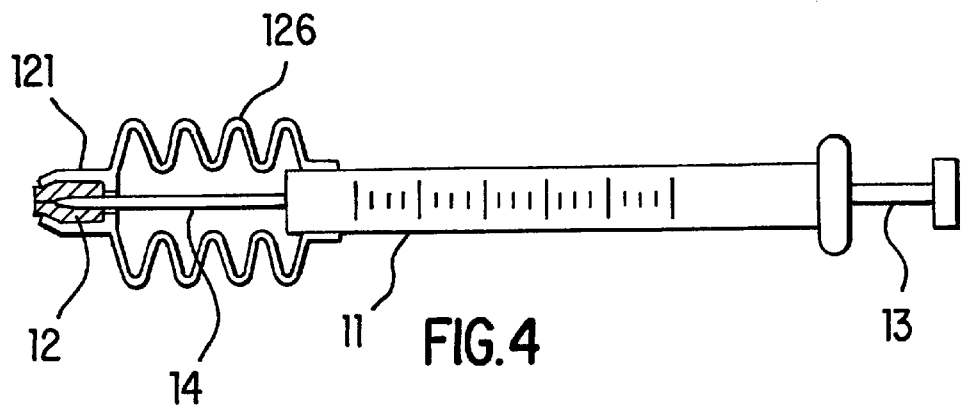
FIG. 4 is an explanatory side view for showing a syringe of a third embodiment of the invention.

FIGS. 3(a) and 4 show second and third embodiments of the invention, and FIG. 3(b) is a sectional view of a guide holder 124 in FIG. 3(a).

In the second embodiment shown in FIG. 3(a), two guide bars 122 are provided. When it is compared with the example shown in FIG. 1(a), more practical function for supporting a tip of a needle on a center axis of a syringe and smoother sliding movement of a plug can be obtained.

In the third embodiment shown in FIG. 4, the bellows 126 made of plastics with a suitable elasticity are integrally formed. Since the elasticity of the material itself is used, a spring need not be provided, separately. Although a function for preventing a needle from being bent can not be expected so much as a rigidity in the horizontal direction of the bellows is poor, no mechanical structure is required. Thus, this type of syringe is suitable for a mass production to thereby reduce its cost.

Figure 5A:
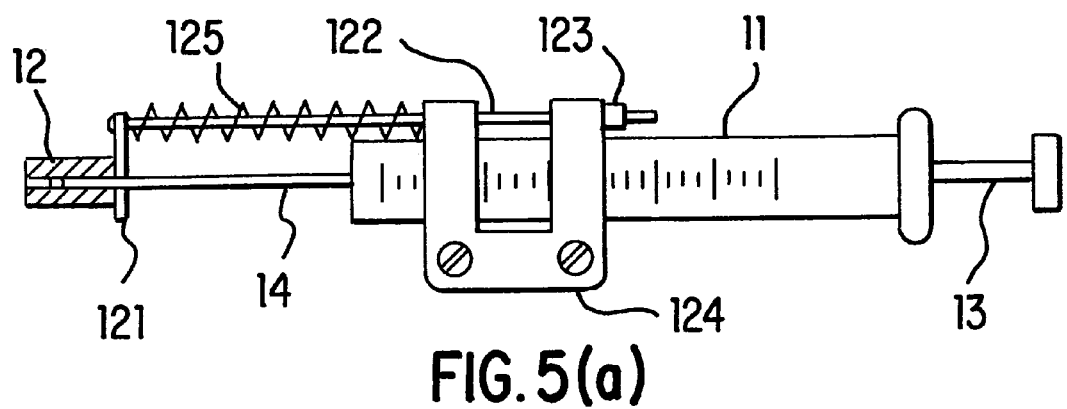
FIG. 5(*a*) is an explanatory side view for showing a syringe of a fourth embodiment of the invention.
Figure 5B:
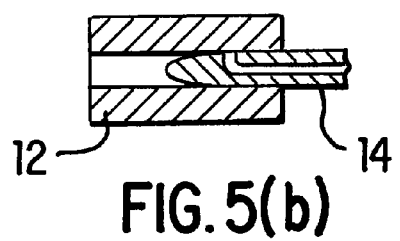

FIG. 5(a) shows a fourth example similar to that shown in FIG. 1(a), and FIG. 5(b) is a sectional view for showing an enlarged structure of a tip of a needle 14.

Figure 6:
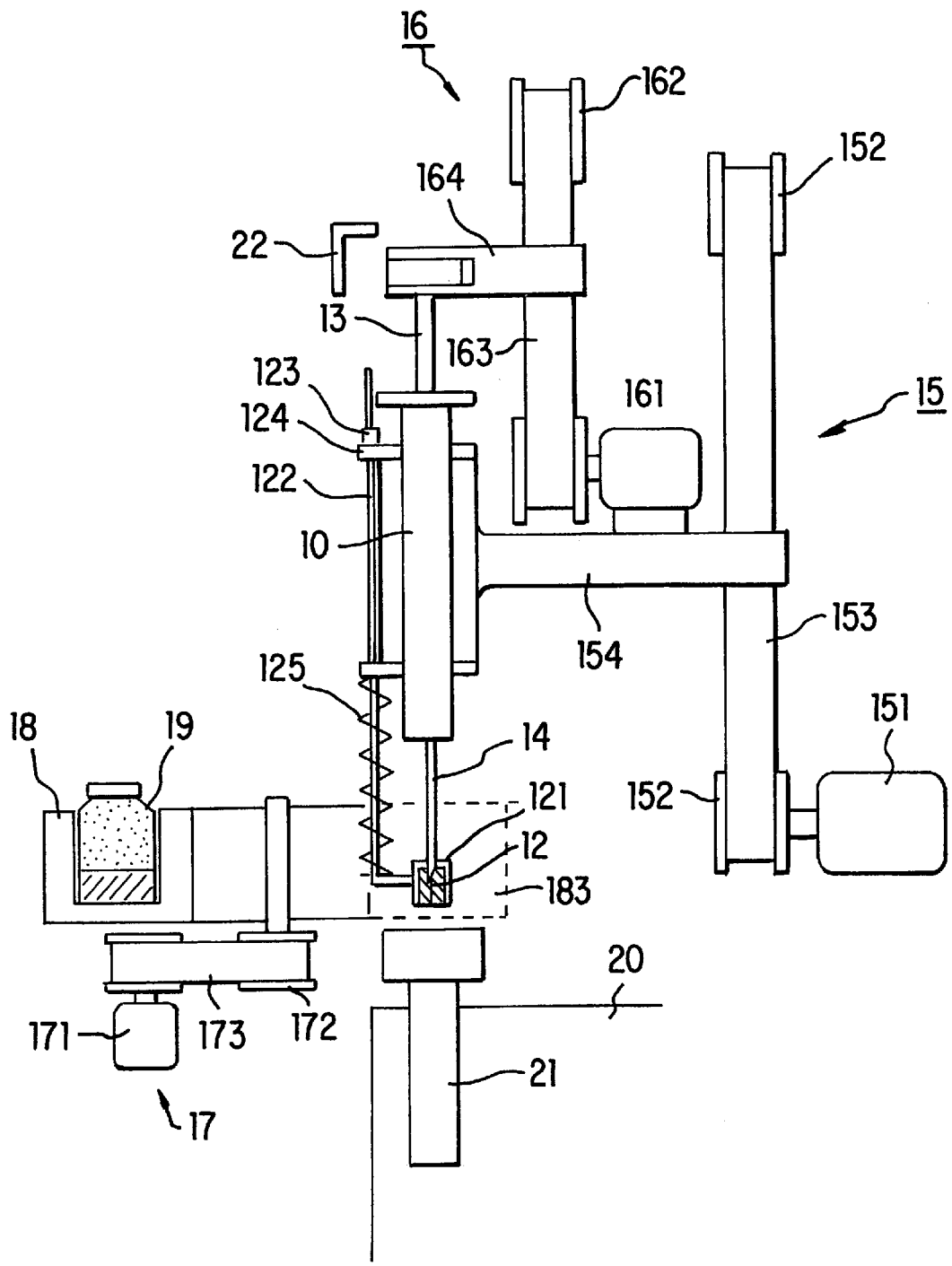
FIG. 6 is an explanatory side view for showing a whole structure of an automatic sampling device of the invention.

FIG. 6 is a diagram for showing a whole structure of an automatic sampling device wherein the syringe of the invention is applied to an automatic sampling device for a gas chromatograph, especially, a head-space automatic sampling device to be used for a gas-type sample. As shown in the drawing, the automatic sampling device of the present embodiment includes a syringe driving mechanism 15 for vertically moving a syringe 10, and a plunger driving mechanism 16 for vertically moving a plunger 13 of the syringe 10. The syringe driving mechanism 15 includes a motor 151 fixed with respect to a sample pouring port 21 of the gas chromatograph 20; a pair of pulleys 152; a belt 153 situated between the pulleys 152; and a syringe damper 154 fixed to a portion of the belt 153.

The plunger driving mechanism 16 is composed of a motor 161 disposed on the syringe damper 154; a pair of pulleys 162 fixed with respect to the syringe damper 154; a belt 163 situated between the pulleys 162; and a plunger damper 164 fixed to a portion of the belt 163.

A plurality of sample bottles 19 (in FIG. 6, only a single bottle is shown) containing samples to be analyzed is mounted on a metal heat-preserving block 18. The heat-preserving block 18 basically has an annular shape provided with a notch 183 for passing the syringe 10 therethrough to thereby have a C-character shape. The heat-preserving block 18 has a plurality of holes for mounting the sample bottles 19.therein, and is driven by a sample driving mechanism 17 including a motor 171, a pair of pulleys 172 and a belt 173.

The syringe 10 has almost the same structure as that shown in FIG. 1, wherein a tip of a needle 14 is inserted into a rubber plug 12 so that a needle opening is closed. The rubber plug 12 is supported by a mechanism including a needle guide 121, guide bar 122, stopper 123, guide holder 124 and spring 125, and can be moved from the tip to a vicinity of a root of the needle 14 along the needle.

The head-space automatic sampling device of the present embodiment as described above is operated as follows in accordance with a program prepared beforehand.

First, a gas or liquid sample to be analyzed (a solid sample may be used, but in the following description the gas or liquid sample is used) is poured or supplied into the sample bottle 19, and the bottle is sealed and mounted in the hole on the heatpreserving block 18.

After the lapse of time in which the sample in the bottle reaches a vapor-liquid equilibrium, the heat-preserving block 18 is rotated by the sample driving mechanism 17, so that the sample bottle 19 is positioned immediately under the syringe 10. The syringe 10 raised at the uppermost position by the last sampling operation is lowered by the syringe driving mechanism 15 and stopped at a position where the needle 14 pierces a septum of the sample bottle 19, and the tip of the needle 14 reaches a space above a liquid surface of the sample in the bottle.

At this time, first, the rubber plug 12 covering the tip of the needle abuts against the septum and, as the syringe is further lowered, only the needle 14 is inserted into the sample bottle 19. Thus, the rubber plug 12 is left on the septum, and slides toward the root of the needle 14, and at the same time the spring 125 is compressed. Next, a gas existing in the upper space of the bottle is sucked into the syringe 10 by raising the plunger 13 through the plunger driving mechanism 16. Subsequently, when the syringe 10 is raised by the syringe driving mechanism 15 to draw the needle 14 out of the sample bottle 19, the rubber plug 12 returns to the tip of the needle 14 by a force of the spring 125 to close the needle opening.

Next, the notch 183 is positioned immediately under the syringe 10 by moving the heat-preserving block 18 through the sample driving mechanism 17. Then, when the syringe 10 is lowered to the lowermost position by the syringe driving mechanism 15, the needle 14 of the syringe 10 passes through the notch 183 and penetrates through the septum provided on an upper portion of the sample pouring port 21. At this time, also, as the needle is penetrated into the septum, the rubber plug 12 is moved toward the needle root. Subsequently, the plunger 13 is lowered by the plunger driving mechanism 16 to inject the taken-in gas into the sample pouring port 21.

Thereafter, the syringe 10 is returned to the uppermost position by the syringe driving mechanism 15 to complete one cycle operation of the automatic sampling device. At this time, also, the rubber plug 12 is immediately returned to the tip of the needle to close the needle opening.

To return the rubber plug 12 to the tip of the needle, instead of the spring 125, a stopper 22 as shown in FIG. 6 may be used. The stopper 22 is located right above the guide bar 122 and is fixed to control a position in a vertical direction. When the syringe 10 is raised by the syringe driving mechanism 15, an upper edge of the guide bar 122 abuts against the stopper 22, and when the syringe 10 is further raised, the guide bar 122 relatively slides downwards with respect to the syringe 10 to thereby move the rubber plug 12 toward the tip of the needle. A position of the stopper 22 is adjusted beforehand so that when the syringe 10 is disposed at the uppermost position, the rubber plug 12 is located to a position to exactly close the needle opening.

In this case, since a force for returning the rubber plug 12 to the needle tip is a force for elevating the syringe 10, in other words, a force of the motor 151 of the syringe driving mechanism 15 which is stronger than a force of the spring, the operation can be positively carried out. On the other hand, in case the rubber plug 12 is returned by the force of the spring 125, when the syringe 10 is raised to draw out the needle 14 from the sample bottle 19, the spring 125 presses down the sample bottle 19 to thereby prevent the sample bottle 19 from being lifted together with the syringe 10. Therefore, it is not necessary to provide a mechanism for pressing the sample bottle 19, separately. The mechanism to be used depends on a design.

In FIG. 6, for the convenience of the description, although both the spring 125 and stopper 22 are shown, it is apparent from the above description that either one of them is used.

Incidentally, it is stated in the above description that the reference numeral 12 designates a "cylindrical rubber plug", but its material is not necessarily rubber, and any soft elastic material similar to rubber can be used. Naturally, its shape need not be limited to the cylindrical shape. Although the rubber plug 12 has a through-hole provided beforehand, a rubber plug without the through-hole may be used so that a through-hole is formed by a syringe.

Further, the above description has been made on the assumption that the hollow needle 14 of a general type has an opening provided at a tip thereof. In case a side-opening needle which is often employed in the head-space gas chromatograph is used, the present invention exhibits more excellent results. More specifically, since the side-opening needle has an opening of the hollow needle on the side surface of the needle, the opening can be easily closed only by lightly inserting the needle into the rubber plug 12. Thus, the socket for compressing the rubber plug from the outside thereof is not required. Also, since no tension acts between the needle guide 121 and the rubber plug 12, it is not necessary to connect them. Therefore, in case of the side-opening needle, a structure for this part can be very simplified. As shown in FIGS. 5(a) and 5(b), it is sufficient that the needle tip is merely inserted into the rubber plug 12 fixed in front of the flat-plate needle guide 121.

As described in detail, in the present invention, the mechanism including the guide for holding the tip of the needle on the center axis of the syringe; the guide mechanism for moving the guide in the area from the tip to the vicinity of the root of the needle; and the plug formed of the soft elastic member into which the needle is inserted and moving with the guide along the needle, is added to a conventional syringe. Since the opening of the needle is closed except when the needle is inserted into a septum of a sample bottle, there is no risk that a sample leaks from the needle opening due to diffusion and air enters thereinto. Also, since the tip of the needle is held by the guide mechanism, there is no risk of bending the needle when the needle is inserted into an object. Moreover, an operation for taking out or pouring a sample can be done in the same manner as that of a conventional syringe to thereby provide an automatic sampling device without troublesome operations.

While the invention has been explained with reference to the specific embodiments of the invention, the explanation is illustrative and the invention is limited only by the appended claims.

What is claimed is:

1. An automatic sampling device, comprising:
   a syringe including a barrel, and a hollow needle attached to the barrel and having an opening at a tip thereof,
   a plug formed of a soft elastic member and slidably engaging the needle to cover at least the opening of the needle, and a guide mechanism situated between the plug and the syringe, said guide mechanism holding the plug to allow the plug to hold the tip of the needle along a center axis of the syringe and to allow the needle to move through the plug between the tip and a root of the needle, said guide mechanism including a needle guide engaging and guiding the needle, to which the plug is attached, and having a side portion for holding the plug, said side portion being partly bent to compress an end portion of the plug so that when the tip of the needle is located in the plug, the opening of the needle is surely closed to prevent passage of a fluid therethrough.

2. An automatic sampling device according to claim 1, wherein said guide mechanism includes bellows having resiliency and situated between the barrel and the needle guide.

3. An automatic sampling device according to claim 1, wherein said plug has a through-hole to allow the needle to pass therethrough, said side portion of the needle guide compressing the through-hole.

4. An automatic sampling device, comprising:

a syringe including a barrel, and a hollow needle attached to the barrel and having an opening at a tip thereof, a plug formed of a soft elastic member and slidably engaging the needle to cover at least the opening of the needle, and a guide mechanism situated between the plug and the syringe, said guide mechanism holding the plug to allow the plug to hold the tip of the needle along a center axis of the syringe and to allow the needle to move through the plug from the tip to a root of the needle, said guide mechanism including a needle guide engaging and guiding the needle, to which the plug is attached, and having a side portion for holding the plug, said side-portion being partly bent to compress an end portion of the plug so that when the tip of the needle is located in the plug, the opening of the needle is closed to prevent passage of a fluid therethrough, a guide holder attached to the barrel, and a guide bar slidably attached to the guide holder, said needle guide being attached to a front end of the guide bar.

5. An automatic sampling device according to claim 4, wherein said guide mechanism further includes a spring attached to the guide holder to urge the needle guide away from the guide holder.

6. An automatic sampling device according to claim 5, wherein said guide bar is formed of two elongated members to sandwich the needle therebetween, said spring being disposed over the needle.

* * * * *